(12) United States Patent
Shalman et al.

(10) Patent No.: US 6,558,334 B2
(45) Date of Patent: May 6, 2003

(54) APPARATUS FOR DIAGNOSING LESION SEVERITY, AND METHOD THEREFOR

(75) Inventors: Evgeny Shalman, Tel Aviv (IL); Alexander Tymonkin, Tel Aviv (IL); Elhanan Dgany, deceased, late of Kfar Saba (IL), by Orly Dgany, executor

(73) Assignee: Florence Medical Ltd., Kfar-Saba (IL)

( * ) Notice: Subject to any disclaimer, the term of this patent is extended or adjusted under 35 U.S.C. 154(b) by 0 days.

(21) Appl. No.: 09/978,179

(22) Filed: Oct. 17, 2001

(65) Prior Publication Data

US 2002/0052553 A1 May 2, 2002

Related U.S. Application Data

(60) Provisional application No. 60/241,333, filed on Oct. 19, 2000.

(51) Int. Cl.$^7$ ................................. A61B 5/02
(52) U.S. Cl. ................. 600/486; 600/485; 600/483
(58) Field of Search ................ 600/486, 485, 600/481, 483, 300

(56) References Cited

U.S. PATENT DOCUMENTS

| | | | | |
|---|---|---|---|---|
| 4,572,199 A | * | 2/1986 | LaCourse | 600/434 |
| 5,715,826 A | | 2/1998 | Horrocks et al. | 128/672 |
| 5,836,884 A | * | 11/1998 | Chio | 600/485 |

FOREIGN PATENT DOCUMENTS

WO    WO 00/53081    9/2000

OTHER PUBLICATIONS

Nico H.J. Pijls, et al. Practice and Potential Pitfalls of Coronary Pressure Measurement; Catheterization and Cardiovascular Interventions 49: 1–16 (2000).

A. Lucian Cousins, M.D. et al.; Prediction of aortic valvular area and gradient by nonivasive techniques; American Heart Journal; Mar., 1978, vol. 95, No. 3.

Mary K. O'boyle et al.; Duplex Sonography of the Carotid Arteries in Patients with Isolated Aoric Stenosis: Imaging Findings and Relation to Severity of Stenosis; AJR:166, Jan. 1995.

Thomas R. Dawber, M.D. et al.; Characteristics of the Dicrotic Notch of the Arterial Pulse Wave in Coronary Heart Disease; Angiology 1973, 2414) pp. 244–255.

Michael l. Oppenheim et al.; An Innovative Dicrotic Notch Detection Algorithm Which Combines Rule–Based Logic with Digital Signal Processing Techniques; Computers and Biomedical Research 28, 154–170 (1995).

Michael Barringer et al.; The Diagnosis of Aortoiliac Disease: A Noninvasive Femoral Cuff Technique; Annals of Surgery 1983, 197 (2) pp. 204–209.

Edward D. Freis, M.D. et al.; Computer Analysis of Carotid and Brachial Pulse Waves:Effects of Age in Normal Subjects; Freis et al. Computer Analysis if Caroted and Brachial Pulse Waves, vol. 28, Nov. 1968 (Available from Nat. Med Library).

\* cited by examiner

*Primary Examiner*—Max F. Hindenburg
*Assistant Examiner*—Navin Natnithithadha
(74) *Attorney, Agent, or Firm*—Nath&Associates PLLC; Harold L. Novick; Marvin C. Berkowitz

(57) ABSTRACT

Apparatus for diagnosing lesion severity of a lesion in an arterial lumen supplying blood to a muscle in its non-hyperemic state of a human subject based on processing information relating to the shape of the dicrotic notch of at least one pressure pulse of his proximal non-hyperemic pressure waveform and either the absence of dicrotic notches along his distal non-hyperemic pressure waveform or the shape of the dicrotic notch of at least one pressure pulse of his distal non-hyperemic pressure waveform if present to calculate the value of a PTC parameter indicative of the severity of the lesion.

24 Claims, 5 Drawing Sheets

APPARATUS FOR DIAGNOSING LESION SEVERITY, AND METHOD THEREFOR

This application is a non-provisional of U.S. provisional application No. 60/241,333 filed Oct. 19, 2000.

FIELD OF THE INVENTION

The invention is in the field of diagnosing lesion severity of a lesion in an arterial lumen of a human subject.

BACKGROUND OF THE INVENTION

Stroke volume pumping by a left ventricle into its adjacent proximal aortic root causes the pressure of the root segment to rise and its wall to distend because it is already filled with blood, thereby creating a high pressure wave which is transmitted into the arteries. The morphology of the aortic pressure waveform corresponds to the three phases of the pressure pulse as follows: Phase I is known as the anacrotic rise occurring during early systole and correlating with the inotropic component, the gradient, and height of the anacrotic rise, and anacrotic notch being related to the rate of acceleration of blood. Phase II appears as a rounded shoulder by virtue of the continued ejection of stroke volume from the left ventricle, displacement of blood, and distension of the arterial walls which produce the rounded appearance. And Phase III appears as a descending limb due to diastolic run-off of blood. This part of the curve normally begins with a dicrotic notch as effected by blood running against the closing aortic valve separating systole from diastole.

A decrease in arterial distensibility occurs with aging and in hypertension, but is most apparent in generalized arteriosclerosis. A decrease in arterial distensibility causes an increase in pulse wave velocity which in turn results in the early return of reflected waves from peripheral sites. These reflected waves fuse with the systolic part of the pulse, leading to increases in pulse pressure, to a late systolic peak in the pulse waveform and disappearance of the diastolic wave, and in particular the dicrotic notch.

Early observations suggested that pressure waveform analysis is useful in evaluating the severity of atherosclerotic vascular disease. Using a classification according to the appearance of the dicrotic notch in the peripheral pressure waveform, it was demonstrated that abnormal pressure waveform with the absence of discrete dicrotic notch is associated with significant atherosclerotic vascular disease. Dawber, T. R., et al, "Characteristics of the dicrotic notch of the arterial pulse wave in coronary heart disease", Angiology, 1973, 24(4): p. 244–55.

More recently, it was shown that abnormalities in the carotid pulse waveform with alteration or disappearance of the dicrotic notch is highly correlated with isolated aortic stenosis. O'Boyle, M. K., et al, "Duplex sonography of the carotid arteries in patients with isolated aortic stenosis: imaging findings and relation to severity of stenosis", American Journal of Roentgenology, 1996, 166(1): p. 197–202. Cousins, A. L., et al "Prediction of aortic valvular area and gradient by noninvasive techniques", American Heart Journal, 1978, 95(3): p. 308–15.

Furthermore, the absence of the dicrotic notch in the pulse pressure waveform distally to aortoiliac disease was almost always associated with significant proximal artery stenosis whereas its presence was found as an excellent index of normal hemodynamics. Barringer, M., et al., "The diagnosis of aortoiliac disease. A noninvasive femoral cuff technique", Annals of Surgery, 1983, 197(2): p. 204–9.

SUMMARY OF THE INVENTION

In accordance with the present invention, there is provided apparatus for diagnosing lesion severity of a lesion in an arterial lumen supplying blood to a muscle in its non-hyperemic state of a human subject, the apparatus comprising:

(a) an intravascular pressure measurement device for deployment adjacent the lesion in the arterial lumen supplying blood to the muscle in its non-hyperemic state;

(b) a pressure monitoring system connected to said intravascular pressure measurement device for measuring a non-hyperemic pressure waveform acquisitioned proximal to the lesion, and a non-hyperemic pressure waveform acquisitioned distal thereto, the former consisting of a series of pressure pulses each including a dicrotic notch, and the latter consisting of a series of pressure pulses each potentially including a dicrotic notch depending on the severity of the lesion; and (c) a Pulse Transmission Coefficient (PTC) processor for processing information relating to the shape of the dicrotic notch of at least one pressure pulse of said proximal non-hyperemic pressure waveform and either the absence of dicrotic notches along said distal non-hyperemic pressure waveform or the shape of the dicrotic notch of at least one pressure pulse of said distal non-hyperemic pressure waveform if present to calculate the value of a PTC parameter indicative of the severity of the lesion.

The present invention is based on the clinical findings that the absence or continuing presence of a dicrotic notch distal to a lesion in an arterial lumen supplying blood to a muscle in its non-hyperemic state significantly correlates to the myocardial fractional flow reserve (FFR) parameter in those instances in which FFR is typically employed to physiologically assess lesion severity but without the need for inducing hyperemia in the muscle as is required for currently employed parameters for physiologically assessing lesion severity, for example, FFR, coronary flow reserve (CFR), and others. On the basis of these findings, the present invention proposes a new parameter for incorporation in blood pressure monitoring apparatus, for example, the SmartFlow™ apparatus commercially available from Florence Medical Ltd, Kfar Saba, Israel, for facilitating the decision making process alongside parameters such as FFR, CFR, and others to determine the necessity of medical treatment of a lesion, and the type of such treatment.

In actual fact, the present invention proposes two alternative parameters PTC(E) and PTC(A) pertaining to different but related characteristics of dicrotic notches. In particular, PTC(E)=Edistal/Eproximal where Edistal is the energy of the high frequency component of the dicrotic notch of a pressure pulse of a human subject's distal non-hyperemic pressure waveform and Eproximal is the energy of the high frequency component of the dicrotic notch of a pressure pulse of his proximal non-hyperemic pressure waveform. While PTC(A)=Adistal/Aproximal where Adistal is the area of a dicrotic notch of a pressure pulse of a human subject's distal non-hyperemic pressure waveform and Aproximal is the area of a dicrotic notch of a pressure pulse of his proximal non-hyperemic pressure waveform. The present invention is suitable for determining lesion severity of lesions in coronary arteries, renal arteries, iliac arteries, carotid arteries, and other arterial lumens.

BRIEF DESCRIPTION OF THE DRAWINGS

In order to understand the invention and to see how it can be carried out in practice, preferred embodiments will now be described, by way of non-limiting examples only, with reference to the accompanying drawings in which.

DETAILED DESCRIPTION OF THE DRAWINGS

Figure 1:
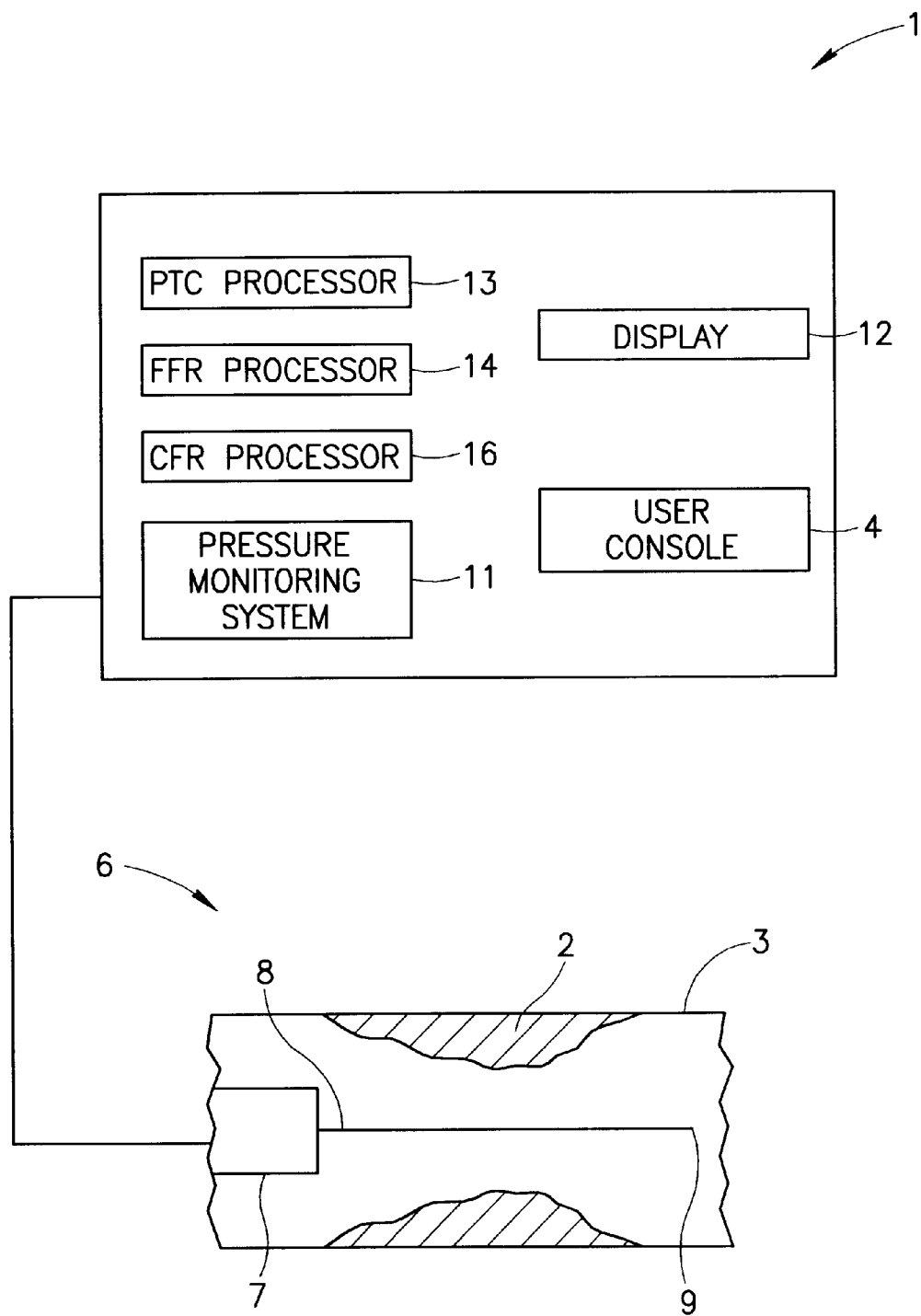
FIG. 1 is a block diagram of apparatus for diagnosing lesion severity of a lesion in an arterial lumen supplying blood to a muscle in its non-hyperemic state of a human subject in accordance with the present invention.

FIG. 1 shows apparatus 1 for diagnosing lesion severity of a lesion 2 in an arterial lumen 3 supplying blood to a muscle in its non-hyperemic state of a human subject to determine the necessity of medical treatment of the lesion, and the type of such treatment. The apparatus 1 is under the control of a user console 4 and includes an intravascular pressure measurement device 6 for acquisitioning pressure waveforms both proximal to the lesion and distal thereto. The intravascular pressure measurement device 6 is preferably implemented as a fluid filled pressure guiding catheter 7 and a pressure guide wire 8 with a pressure transducer 9 at its tip, thereby enabling simultaneous acquisition of both pressure waveforms. An exemplary pressure guiding catheter 7 is the Ascent JL4 catheter commercially available from Medtronic, USA, whilst an exemplary pressure guide wire 8 is the PressureWire™ pressure guide wire commercially available from Radi Medical, Uppsala, Sweden.

Figure 2:
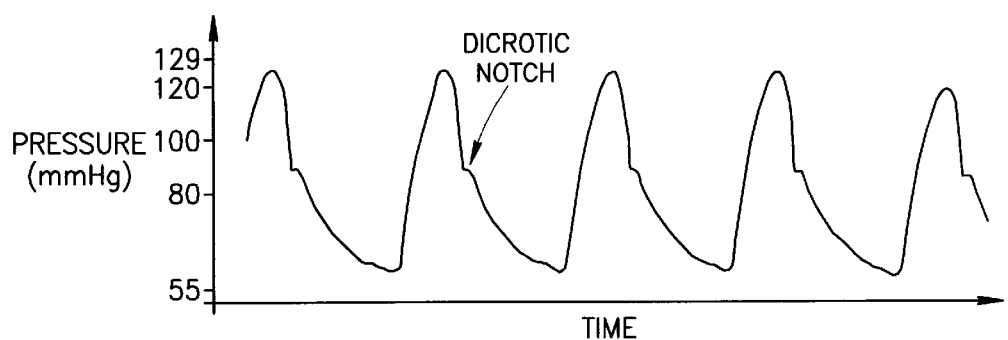
FIG. 2 is a graph showing an exemplary pressure waveform of a series of pressure pulses acquisitioned proximal to either a severe or a non-severe lesion.
Figure 3:
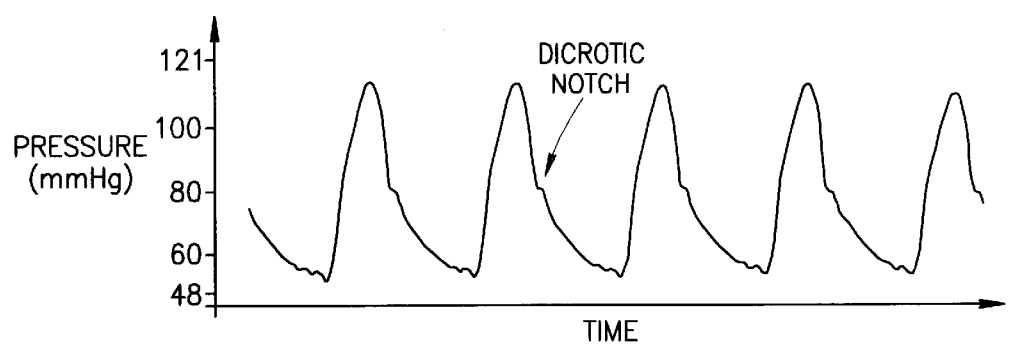
FIG. 3 is a graph showing an exemplary pressure waveform of a series of pressure pulses acquisitioned distal to a non-severe lesion.
Figure 4:
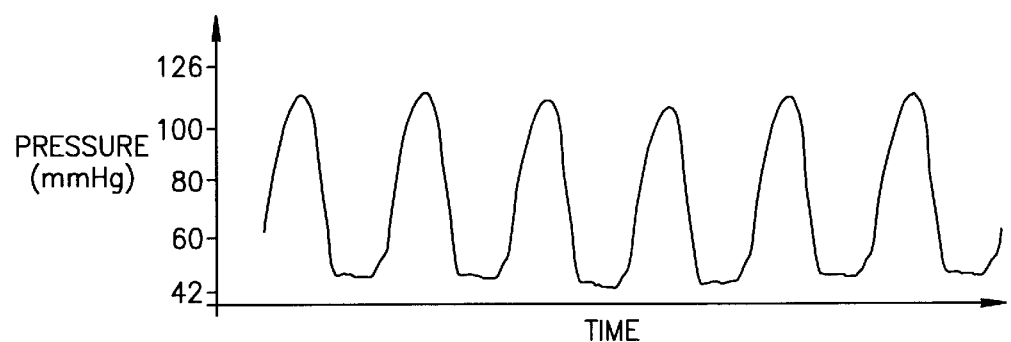
FIG. 4 is a graph showing an exemplary pressure waveform of a series of pressure pulses acquisitioned distal to a severe lesion.

The apparatus 1 includes a pressure monitoring system 11 connected to the intravascular pressure measurement device 6 for measuring pressure waveforms acquisitioned proximal and distal to the lesion for display on a display 12. FIG. 2 depicts an exemplary pressure waveform acquisitioned proximal to a lesion in an arterial lumen supplying blood to a muscle in its non-hyperemic state, the pressure waveform consisting of a series of pressure cycles each having a dicrotic notch which typically continue distal to a non-severe lesion (see FIG. 3), and typically discontinue distal to a severe lesion (see FIG. 4). The apparatus 1 includes a PTC processor 13 programmed for calculating the value of one of a PTC(E) parameter or a PTC(A) parameter also for display on the display 12. The apparatus 1 may also include a FFR processor 14 for displaying the value of the FFR parameter, and a CFR processor 16 for displaying the value of a CFR parameter, for example, as illustrated and described in Applicant's WO 00/53081 entitled "A Method and System for Pressure Based Measurements of CFR and Additional Hemodynamic Parameters".

Figure 5:
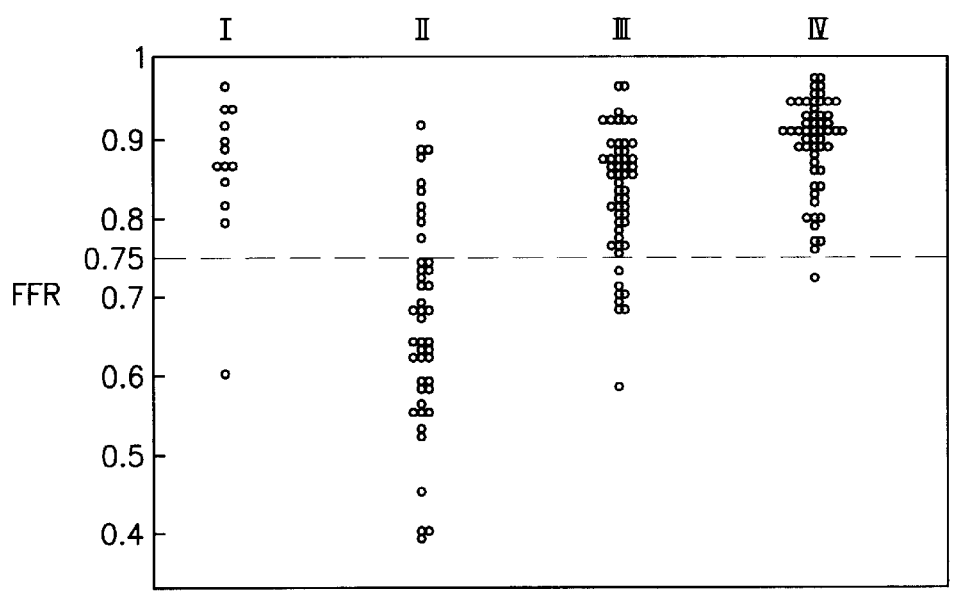
FIG. 5 is a graph showing the results of an experiment for demonstrating the correlation between the continuing distal presence of a dicrotic notch with FFR for predicting the need for intervention.

FIG. 5 shows the results of an experiment for correlating between the continuing distal presence of a dicrotic notch and the threshold FFR value 0.75 which is most often (approximately 95%) associated with stenosis requiring intervention such as stenting or balloon dilatation. The human subjects were classified into four groups as follows: Group I (about 10%) in which subjects do not demonstrate dicrotic notches neither in their proximal pressure waveforms nor in their distal pressure waveforms typically indicating other clinical problems, or wrong clinical setting during catheterization procedure such as the catheter blocking blood flow. Group II in which subjects demonstrate dicrotic notches in their proximal pressure waveforms but not in their distal pressure waveforms. Group III in which subjects demonstrate dicrotic notches both in their proximal pressure waveforms and in their distal pressure waveforms. And Group IV in which subjects demonstrate dicrotic notches in their proximal pressure waveforms, in their distal pressure waveforms, and in their distal hyperemic pressure waveforms after vasodilatation. FIG. 5 shows that Groups II and III have a relatively high correlation with FFR for predicting the need for intervention on the basis of the continuing presence of a dicrotic notch distal to a lesion.

Calculation of PTC(E) Using Filtered Pressure Waveform

Figure 6:
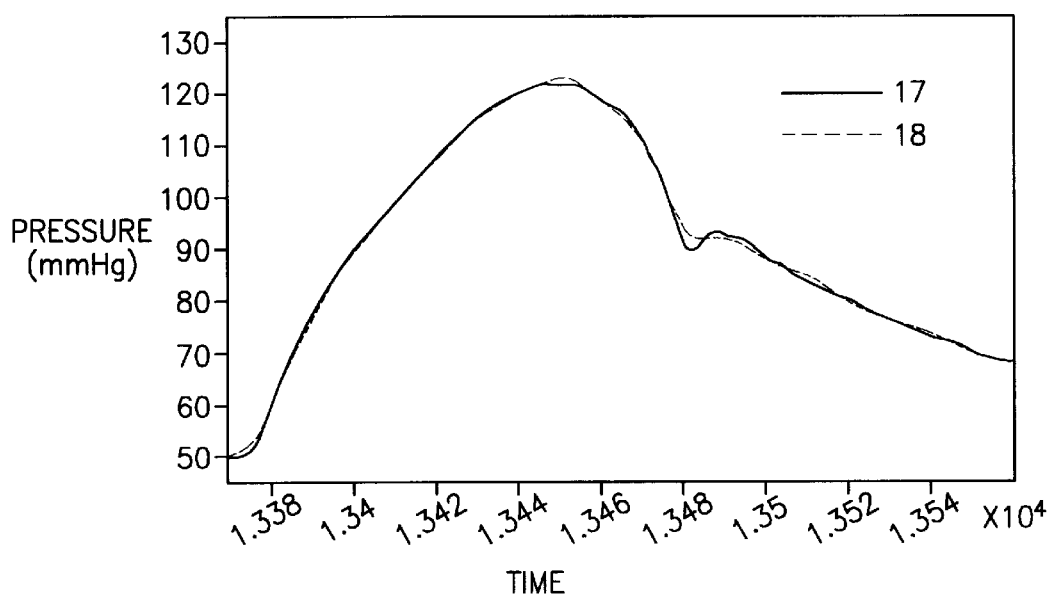
FIG. 6 is a graph showing an exemplary measured pressure waveform P(t) and its low pass filtered derivative Plow(t)
Figure 7:
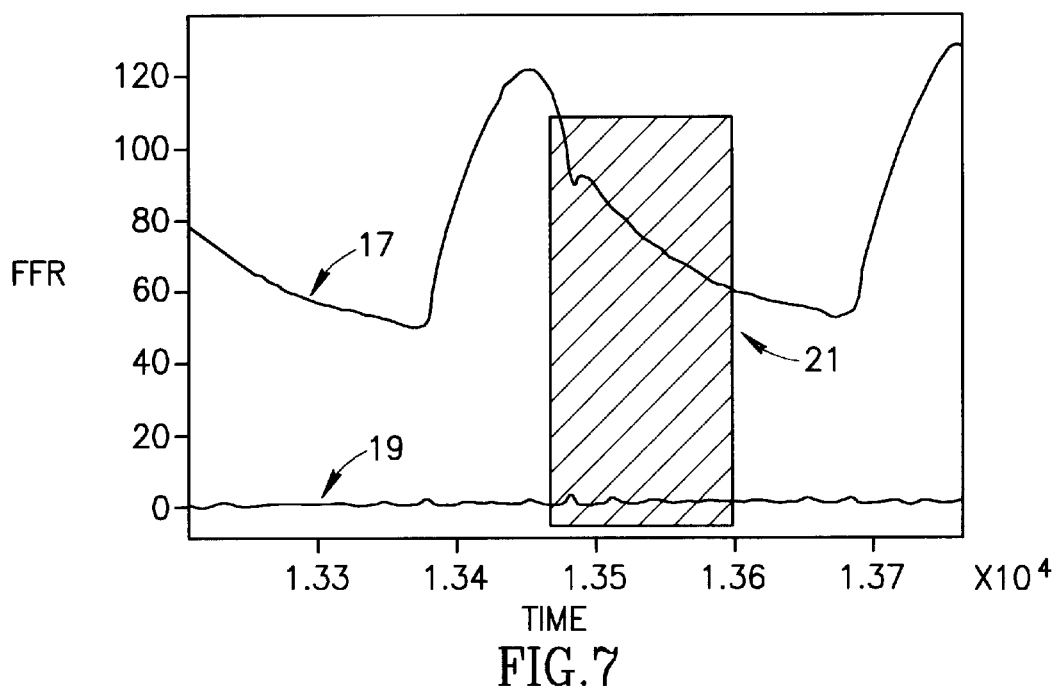
FIG. 7 is a graph showing the measured pressure waveform P(t) of FIG. 6 and the function dP(t) where dP(t)=P(t)−Plow(t) for calculating the value of the PTC(E) parameter in accordance with the present invention.

The present invention proposes a first PTC(E) parameter as follows:

PTC(E)=Edistal/Eproximal where Edistal is the energy of the high frequency component of the dicrotic notch of a pressure pulse of a human subject's distal non-hyperemic pressure waveform and Eproximal is the energy of the high frequency component of the dicrotic notch of a pressure pulse of his proximal non-hyperemic pressure waveform. The energy of the high frequency component of the dicrotic notch of a pressure pulse is given by the standard deviation of dP(t) where dP(t)=P(t)−Plow(t), P(t) being a measured pressure pulse and Plow(t) its low pass filtered derivative containing only the first 6 harmonics of the measured pressure waveform P(t). FIG. 6 shows a graph with a measured pressure waveform P(t) 17 (full line) and its low pass filtered derivative Plow(t) 18 (dotted line). FIG. 7 shows the differential pressure waveform dP(t) 19 and an exemplary Region Of Interest (ROI) 21 for calculating the energy of the high frequency component of a dicrotic notch. Other high frequency components of the differential pressure waveform dP(t) can be observed at the occurrences of maximum pressure and minimum pressure.

The use of the apparatus 1 for calculating the value of the PTC(E) parameter in respect of a lesion under investigation is as follows:

The fluid filled pressure guiding catheter 7 is introduced proximal to the lesion under investigation. The pressure guide wire 8 is introduced into the catheter 7 such that its pressure transducer 9 lies flush with the catheter's tip. The apparatus 1 is calibrated such that both the catheter 7 and the pressure guide wire 8 give the same pressure reading. The pressure guide wire's pressure transducer 9 is extended distally beyond the lesion under investigation. Without inducing hyperemia in the muscle supplied by the arterial lumen suffering from the lesion under investigation, the apparatus 1 acquisitions pressure waveforms both proximal and distal thereto. The ROIs for the calculation of Edistal and Eproximal may be determined manually or automatically using zeroes of the function dP(t) before invoking the PCT processor 13 to calculate the value of the PCT(E) parameter for display on the display 12.

Figure 8:
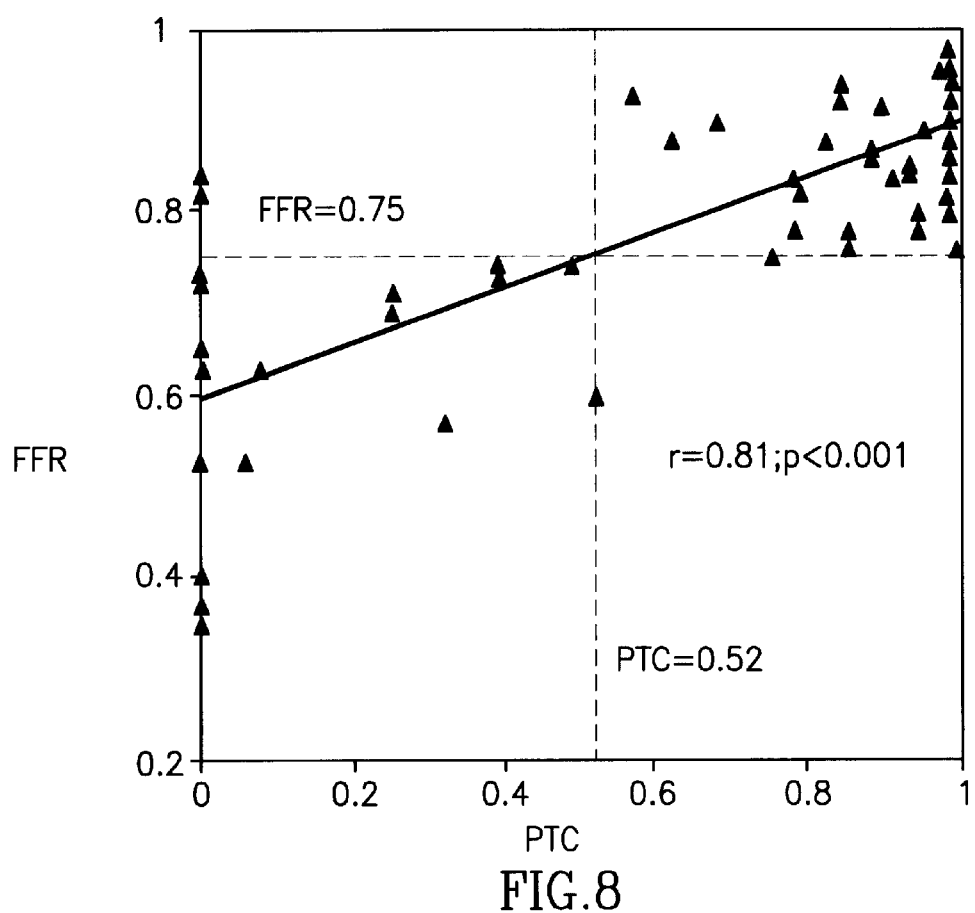
FIG. 8 is a graph showing the correlation between PTC(E) and FFR for clinical trials.

Clinical trials have shown that there is a significant correlation between the PTC and FFR (r=0.81, p<0.001; see FIG. 8 published in The American Journal of Cardiology, Sep. 11, 2001). By using a receiver-operating characteristic (ROC) curve analysis, in the overall cohort of 118 observations, PTC(E)<0.52 (sensitivity 100%, specificity 98%) was found to be the optimal cut-off value for predicting FFR<0.75.

Calculation of PTC(A) as a Function of Area of Dicrotic Notch

Figure 9:
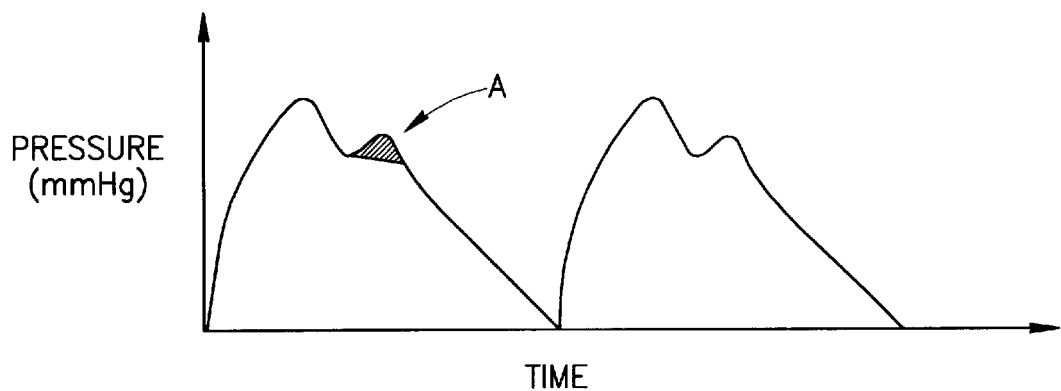
FIG. 9 is a pictorial representation showing the area of a dicrotic notch for calculating the value of the PTC(A) parameter in accordance with the present invention.
Figure 10:
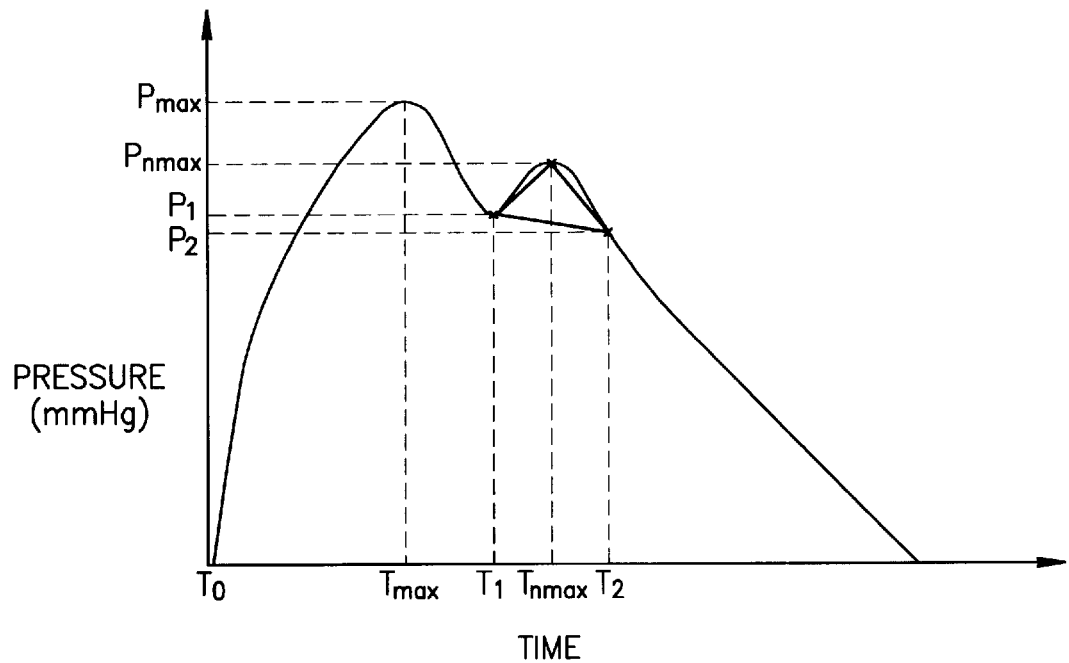
FIG. 10 is a pictorial representation showing the approximation of the area of a dicrotic notch to that of a scalene triangle.

The present invention proposes a second PTC parameter PTC(A) as follows: PTC(A)=Adistal/Aproximal where Adistal is the area of the dicrotic notch of a pressure pulse of a human subject's distal non-hyperemic pressure waveform and Aproximal is the area of the dicrotic notch of a pressure pulse of his proximal non-hyperemic pressure waveform (see FIG. 9). For computational ease, the area A of the dicrotic notch of a pressure pulse is approximated as that of a scalene triangle having vertices which lie thereon. The co-ordinates of the vertices are as follows: (T1,P1) where T1 corresponds to the occurrence of the first local post systolic minimum of the pressure pulse; (Tnmax,Pnmax) corresponds to the occurrence of the local maximum pressure of the dicrotic notch; and (T2,P2) where T2=T1+(Tmax−T0)/3 where Tmax corresponds to the occurrence of maximum pressure Pmax of the pressure pulse, and T0 corresponds to the occurrence of minimum pressure (see FIG. 10). The use of apparatus 1 for calculating the value of the PTC(A) parameter in respect of a lesion under investigation is similar to the use of the apparatus 1 for calculating the value of PCT(E) described hereinabove. Clinical trials have shown that PTC(A)<0.25 is the best threshold value for predicting FFR<0.75.

While the invention has been described with respect to a limited number of embodiments, it will be appreciated that many variations, modifications, and other applications of the invention can be made within the scope of the appended claims. For example, a Plow(t) low pass filtered derivative can contain between five to seven of the first harmonics of the measured pressure waveform P(t).

What is claimed is:

1. Apparatus for diagnosing lesion severity of a lesion in an arterial lumen supplying blood to a muscle in its non-hyperemic state of a human subject, the apparatus comprising:
   (a) an intravascular pressure measurement device for deployment adjacent the lesion in the arterial lumen supplying blood to the muscle in its non-hyperemic state;
   (b) a pressure monitoring system connected to said intravascular pressure measurement device for measuring a non-hyperemic pressure waveform acquisitioned proximal to the lesion, and a non-hyperemic pressure waveform acquisitioned distal thereto, the former consisting of a series of pressure pulses each including a dicrotic notch, and the latter consisting of a series of pressure pulses each potentially including a dicrotic notch depending on the severity of the lesion; and
   (c) a Pulse Transmission Coefficient (PTC) processor for processing information relating to the shape of the dicrotic notch of at least one pressure pulse of said proximal non-hyperemic pressure waveform and either the absence of dicrotic notches along said distal non-hyperemic pressure waveform or the shape of the dicrotic notch of at least one pressure pulse of said distal non-hyperemic pressure waveform if present to calculate the value of a PTC parameter indicative of the severity of the lesion.

2. Apparatus according to claim 1 wherein said PTC parameter is denoted PTC(E) where PTC(E) α Edistal/Eproximal, Edistal being the energy of the high frequency component of the dicrotic notch of a pressure pulse of the distal non-hyperemic pressure waveform and Eproximal being the energy of the high frequency component of the dicrotic notch of a pressure pulse of the proximal non-hyperemic pressure waveform.

3. Apparatus according to claim 2 wherein the energy of the high frequency component of the dicrotic notch of a pressure pulse is given by the standard deviation of dP(t) where dP(t)=P(t)−Plow(t), P(t) being a measured pressure pulse and Plow(t) its low pass filtered derivative.

4. Apparatus according to claim 3 wherein said low pass filtered derivative Plow(t) contains between five to seven of the first harmonics of said measured pressure pulse P(t).

5. Apparatus according to claim 4 wherein said low pass filtered derivative Plow(t) contains the first six harmonics of said measured pressure pulse P(t).

6. Apparatus according to claim 1 wherein said PTC parameter is denoted PTC(A) where PTC(A) α Adistal/Aproximal, Adistal being the area of the dicrotic notch of a pressure pulse of said distal non-hyperemic pressure waveform and Aproximal being the area of the dicrotic notch of a pressure pulse of said proximal non-hyperemic pressure waveform.

7. Apparatus according to claim 6 wherein the area of the dicrotic notch of a pressure pulse is approximated as the area of a triangle whose vertices lie thereon.

8. Apparatus according to claim 7 wherein the vertices of the triangle are as follows: (T1,P1) where T1 corresponds to the occurrence of the first local post systolic minimum of the pressure pulse; (Tnmax,Pnmax) corresponds to the occurrence of the local maximum pressure of the dicrotic notch; and (T2,P2) where T2=T1+(Tmax−T0)/3 where Tmax corresponds to the occurrence of maximum pressure Pmax of the pressure pulse, and T0 corresponds to the occurrence of minimum pressure.

9. A method for diagnosing lesion severity of a lesion in an arterial lumen supplying blood to a muscle in its non-hyperemic state of a human subject, the method comprising the steps of:
   (a) deploying an intravascular pressure measurement device adjacent the lesion in the arterial lumen supplying blood to the muscle in its non-hyperemic state;
   (b) measuring a non-hyperemic pressure waveform acquisitioned proximal to the lesion, and a non-hyperemic pressure waveform acquisitioned distal thereto, the former consisting of a series of pressure pulses each including a dicrotic notch, and the latter consisting of a series of pressure pulses each potentially including a dicrotic notch depending on the severity of the lesion; and
   (c) processing information relating to the shape of the dicrotic notch of at least one pressure pulse of the proximal non-hyperemic pressure waveform and either the absence of the dicrotic notches along the distal non-hyperemic pressure waveform or the shape of the dicrotic notch of at least one pressure pulse of the distal non-hyperemic pressure waveform if present to calculate the value of a PTC parameter indicative of the severity of the lesion.

10. The method according to claim 9 wherein the PTC parameter is denoted PTC(E) where PTC(E) α Edistal/Eproximal, Edistal being the energy of the high frequency component of the dicrotic notch of a pressure pulse of the distal non-hyperemic pressure waveform and Eproximal being the energy of the high frequency component of the dicrotic notch of a pressure pulse of the proximal non-hyperemic pressure waveform.

11. The method according to claim 10 wherein the energy of the high frequency component of the dicrotic notch of a pressure pulse is given by the standard deviation of dP(t) where dP(t)=P(t)−Plow(t), P(t) being the measured pressure pulse and Plow(t) its low pass filtered derivative.

12. The method according to claim 11 wherein the low pass filtered derivative Plow(t) contains between five to seven the first harmonics of the measured pressure pulse P(t).

13. The method according to claim 12 wherein the low pass filtered derivative Plow(t) contains the first six harmonics of the measured pressure pulse P(t).

14. The method according to claim 9 wherein the PTC parameter is denoted PTC(A) where PTC(A) α Adistal/Aproximal, Adistal being the area of the dicrotic notch of a pressure pulse of the distal non-hyperemic pressure waveform and Aproximal being the area of the dicrotic notch of a pressure pulse of the proximal non-hyperemic pressure waveform.

15. The method according to claim 14 wherein the area of the dicrotic notch of a pressure pulse is approximated as the area of a triangle whose vertices lie thereon.

16. The method according to claim 15 wherein the vertices of the triangle are as follows: (T1,P1) where T1 corresponds to the occurrence of the first local post systolic minimum of the pressure pulse; (Tnmax,Pnmax) corresponds to the occurrence of the local maximum pressure of the dicrotic notch; and (T2,P2) where T2=T1+(Tmax−T0)/3 where Tmax corresponds to the occurrence of maximum pressure Pmax of the pressure pulse, and T0 corresponds to the occurrence of minimum pressure.

17. For use with intravascular pressure measurement apparatus capable of acquisitioning pressure measurements proximal to a lesion in a lesioned blood vessel and distal thereto in its non-hyperemic state, a Pulse Transmission Coefficient (PTC) processor for diagnosing lesion severity, the PTC processor capable of executing the following steps:

(a) processing information relating to the shape of the dicrotic notch of at least one pressure pulse of a proximal non-hyperemic pressure waveform;

(b) processing information relating to the shape of the dicrotic notch of at least one pressure pulse of a distal non-hyperemic pressure waveform if present; and (c) calculating the value of a PTC parameter indicative of the severity of the lesion.

18. The CFR processor according to claim 17 wherein the PTC parameter is denoted PTC(E) where PTC(E) Edistal/Eproximal, Edistal being the energy of the high frequency component of the dicrotic notch of a pressure pulse of the distal non-hyperemic pressure waveform and Eproximal being the energy of the high frequency component of the dicrotic notch of a pressure pulse of the proximal non-hyperemic pressure waveform.

19. The CFR processor according to claim 18 wherein the energy of the high frequency component of the dicrotic notch of a pressure pulse is given by the standard deviation of dP(t) where dP(t)=P(t)−Plow(t), P(t) being a measured pressure pulse and Plow(t) its low pass filtered derivative.

20. The CFR processor according to claim 19 wherein the low pass filtered derivative Plow(t) contains between five to seven of the first harmonics of the measured pressure pulse P(t).

21. The CFR processor according to claim 20 wherein the low pass filtered derivative Plow(t) contains the first six harmonics of the measured pressure pulse P(t).

22. The CFR processor according to claim 17 wherein the PTC parameter is denoted PTC(A) where PTC(A) Adistal/Aproximal, Adistal being the area of the dicrotic notch of a pressure pulse of the distal non-hyperemic pressure waveform and Aproximal being the area of the dicrotic notch of a pressure pulse of the proximal non-hyperemic pressure waveform.

23. The CFR processor according to claim 22 wherein the area of the dicrotic notch of a pressure pulse is approximated as the area of a triangle whose vertices lie thereon.

24. The CFR processor according to claim 23 wherein the vertices of the triangle are as follows: (T1,P1) where T1 corresponds to the occurrence of the first local post systolic minimum of the pressure pulse; (Tnmax, Pnmax) corresponds to the occurrence of the local maximum pressure of the dicrotic notch; and (T2,P2) where T2=T1+(Tmax−T0)/3 where Tmax corresponds to the occurrence of maximum pressure P max of the pressure pulse, and T0 corresponds to the occurrence of minimum pressure.

* * * * *